US006228330B1

(12) United States Patent
Herrmann et al.

(10) Patent No.: US 6,228,330 B1
(45) Date of Patent: May 8, 2001

(54) ATMOSPHERIC-PRESSURE PLASMA DECONTAMINATION/STERILIZATION CHAMBER

(75) Inventors: Hans W. Herrmann; Gary S. Selwyn, both of Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/328,169

(22) Filed: Jun. 8, 1999

(51) Int. Cl.[7] .......... B01J 19/12
(52) U.S. Cl. .......... 422/186.05; 422/907
(58) Field of Search .......... 422/186.05, 907

(56) References Cited

U.S. PATENT DOCUMENTS

| | | | | |
|---|---|---|---|---|
| 935,457 | * | 9/1909 | Bridge | 422/186.05 |
| 3,453,469 | * | 7/1969 | Cann et al. | 422/186.07 |
| 3,775,621 | * | 11/1973 | Gorin | 422/186.05 |
| 4,430,306 | * | 2/1984 | Namba et al. | 422/292 |
| 5,977,715 | * | 11/1999 | Li et al. | 315/111.51 |

OTHER PUBLICATIONS

Schutze et al., "The Atmospheric–Pressure Plasma Jet: A Review and Comparison to Other Plasma Sources," IEEE Trans. Plasma Sci. 26, 1685 (1998).*

H.W. Herrman et al., "Decontamination of chemical and biological warfare (CBW) agents using an atmospheric pressure plasma jet (APPJ)," Phys. Plasmas 6, 2284 (1999).*

K. Kelly–Wintenberg et al., "Room Temperature Sterilization of Surfaces and Fabrics with a One Atmosphere Uniform Glow Discharge Plasma," J. Indust. Microbio. & Biotech. 20, 69 (1998) No month available.

* cited by examiner

*Primary Examiner*—Kathryn Gorgos
*Assistant Examiner*—Thao Tran
(74) *Attorney, Agent, or Firm*—Samuel M. Freund

(57) ABSTRACT

An atmospheric-pressure plasma decontamination/sterilization chamber is described. The apparatus is useful for decontaminating sensitive equipment and materials, such as electronics, optics and national treasures, which have been contaminated with chemical and/or biological warfare agents, such as anthrax, mustard blistering agent, VX nerve gas, and the like. There is currently no acceptable procedure for decontaminating such equipment. The apparatus may also be used for sterilization in the medical and food industries. Items to be decontaminated or sterilized are supported inside the chamber. Reactive gases containing atomic and metastable oxygen species are generated by an atmospheric-pressure plasma discharge in a $He/O_2$ mixture and directed into the region of these items resulting in chemical reaction between the reactive species and organic substances. This reaction typically kills and/or neutralizes the contamination without damaging most equipment and materials. The plasma gases are recirculated through a closed-loop system to minimize the loss of helium and the possibility of escape of aerosolized harmful substances.

8 Claims, 3 Drawing Sheets

ATMOSPHERIC-PRESSURE PLASMA DECONTAMINATION/STERILIZATION CHAMBER

STATEMENT REGARDING FEDERAL RIGHTS

This invention was made with government support under Contract No. W-7405-ENG-36 awarded by the U.S. Department of Energy to The Regents of The University of California. The government has certain rights in the invention.

FIELD OF THE INVENTION

The present invention relates generally to the decontamination and/or sterilization of sensitive articles such as electronics, optics and art works, to identify three examples, which have been contaminated by chemical and/or biological warfare agents and biological pathogens and, more particularly, to the decontamination and/or sterilization of these articles using a contained, atmospheric-pressure plasma.

BACKGROUND OF THE INVENTION

There are currently no acceptable methods for decontaminating sensitive equipment such as electronics, optics, and artworks which have been exposed to chemical or biological warfare (CBW) agents including anthrax, mustard blistering agent, VX nerve gas, and the like. Current candidate technologies include: (1) solvent washing; (2) low-pressure plasmas; (3) supercritical carbon dioxide ($SCCO_2$); (4) reactive foams and gels; and (5) atmospheric-pressure plasmas. Solvent washing uses chlorinated fluorocarbon replacement solvents to remove CBW agents, thereby contaminating the solvent and necessitating frequent replacement and decontamination or acceptable disposal of the solvent. It is also unclear how effective this method is, particularly against biological warfare agents. Low-pressure plasmas have potential but, typically, are not very penetrating and are limited to materials that can survive being subjected to a vacuum. At sub-torr pressures, reactive species must rely on diffusion to penetrate into cavities and crevices which are often beyond the spread of the plasma, thereby restricting this procedure's usefulness for other than smooth, vacuum-compatible objects having only external contamination. By employing pressure pulsing to pressures above about 100 torr in a decontamination chamber, convection will augment the transport of reactive species, thereby enhancing penetration into cavities and crevices. Supercritical $CO_2$ has shown promise for removal of chemical warfare agents; however, this process requires secondary separation and neutralization of the agent. Moreover, the high pressure of the super-critcal point (~73 atm) may restrict the types of materials that can be decontaminated. Hermetically sealed equipment and certain polymers, as examples, are at risk. Reactive foams and gels may be of use, but aqueous content and lingering residues may degrade performance of sensitive equipment.

The standard for sterilization involves steam treatment at 121° C. and 15 psi above atmospheric pressure in an autoclave. This procedure can be used only for articles which can withstand moisture and heat under pressure, and excludes materials and equipment such as endoscopes and surgical sharps. Dry heat at 165° C. may be used for moisture-sensitive but not heat-sensitive materials. Ethylene oxide (EtO) is the industry standard for low-temperature sterilization, but also raises many difficulties. Hospitals have been reducing their dependence on EtO due to its extreme toxicity, flammability and environmental consequences. Furthermore, a sterilization cycle using EtO takes approximately 18 hours to complete and is expensive and inconvenient, since highly trained operators are required. Ionizing radiation has been accepted for certain applications; however, public concern over safety and the environment continue to be issues which must be overcome. Liquid disinfectants, such as peracetic acid, cannot be used on moisture-sensitive materials and are hazardous, which leads to environmental concerns regarding their disposal. Low-pressure hydrogen peroxide plasma sterilization has recently been introduced. It is thought that hydrogen peroxide vapor is solely responsible for the sterilization, while the plasma merely decomposes the hydrogen peroxide after the sterilization process so that residuals are not left on surfaces. Again, this process cannot be used for moisture-sensitive materials and, as stated hereinabove, low-pressure plasmas are not attractive for sterilization due to the poor penetration capability of the short-lived reactive species by diffusion processes, the requirement that the materials be vacuum-compatible, and the cost of vacuum generating equipment.

Atmospheric-pressure plasmas are useful for both removal of unwanted materials from substrates and neutralization/ sterilization thereof without damaging most substrates. As a sterilization method for the health care and food industries, atmospheric pressure plasmas offer many advantages over existing methods. Atmospheric pressure plasmas can be non-thermal (cold) plasmas, or thermal (hot) plasmas. Traditional cold atmospheric-pressure plasmas, such as the corona discharge and the dielectric-barrier or silent-discharge plasma, are highly non-uniform and are typically used for volume processing of gaseous effluents or as ozone generators. Emerging cold atmospheric-pressure technologies include a one atmosphere uniform glow discharge plasma described in "Room Temperature Sterilization of Surfaces And Fabrics With A One Atmosphere Uniform Glow Discharge Plasma" by K. Kelly-Wintenberg et al., J. Indust. Microbio. & Biotech. 20, 69 (1998). This device generates a uniform plasma and, in the case of oxygen containing plasmas, favors the preferable production of atomic oxygen over ozone. However, only low-power densities can be achieved.

The atmospheric-pressure plasma jet (APPJ) is a non-thermal, high-pressure uniform-glow plasma discharge that produces a high-velocity effluent stream of reactive chemical species. See, e.g., "The Atmospheric-Pressure Plasma Jet: A Review And Comparison To Other Plasma Sources" by A. Schutze et al., IEEE Trans. Plasma Sci. 26, 1685 (1998). The discharge operates on a feedstock gas such as $He/O_2/H_2O$, which flows between an outer, grounded, cylindrical electrode and an inner, coaxial electrode powered at 13.56 MHz. While passing through the plasma, the feedstock gas becomes excited, dissociated or ionized by electron impact. Once the gas exits the discharge volume, ions and electrons are rapidly lost by recombination, but the fast-flowing effluent still contains neutral metastable species (for example, $O_2^*$ and $He^*$) and radicals (for example, O and OH).

The use of the atmospheric-pressure plasma jet for decontamination of chemical and biological warfare agents is described in "Decontamination Of Chemical And Biological Warfare (CBW) Agents Using An Atmospheric Pressure Plasma Jet (APPJ)" by H. W. Herrmann et al., Phys. Plasmas 6, 2284 (1999). The reactive effluent from an APPJ has been shown to be an effective neutralizer of surrogates for anthrax spores and mustard blistering agent. Unlike conventional decontamination methods, the plasma effluent was observed not to cause corrosion or destroy wiring, electronics, or most plastics, rendering it suitable for decontamination of sensitive equipment and interior spaces. Furthermore, the reactive species in the effluent were observed to degrade into harmless products leaving no residues or harmful by-products. The APPJ can be run at high power densities, unlike other cold discharges, which results in higher fluxes of reactive species.

Hot atmospheric-pressure plasmas, such as dc arc jets and rf plasma torches, operate at several thousand degrees Celsius which is too hot for most decontamination applications. Although the APPJ operates at somewhat higher temperatures than other cold discharges, APPJ exposure temperatures can be maintained in an acceptable range for most decontamination applications (that is, between 50° C. and 300° C.). Moreover, these slightly elevated temperatures often produce a desirable effect by increasing reaction rates.

Unlike the other cold atmospheric-pressure plasmas, the APPJ requires helium in the feedstock gas. The feedstock is vented to areas surrounding the APPJ, thereby permitting the helium to irretrievably escape as well as allowing the escape of re-aerosolized agents or harmful byproducts thereof. Although operation of an APPJ using an alternative feed gas, such as air, may be possible, there have been no reports of such operation.

Accordingly, it is an object of the present invention to provide an atmospheric-pressure plasma sterilization chamber capable of minimizing loss of helium.

Another object of the present invention is to provide an atmospheric-pressure plasma sterilization chamber capable of recirculating the helium from the feedstock gas and preventing the escape of re-aerosolized agents or harmful byproducts thereof.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for decontaminating or sterilizing articles hereof includes: a gas-tight chamber; a first conducting cylindrical electrode disposed within the chamber; a radiofrequency power supply in electrical contact with the first electrode for providing radiofrequency energy thereto; a grounded, second conducting cylindrical electrode disposed within the first electrode and collinear therewith and having holes throughout its surface, whereby an annular region is formed between the two electrodes, and the article to be decontaminated or sterilized being located within the interior of the second electrode; and means for introducing gases into the chamber such that the introduced gas flows directly into the annular region and exits this region through the holes in the second electrode, whereby a uniform radiofrequency electrical discharge occurs in the gas flowing through the annular region as a result of the radiofrequency energy having been applied to the first electrode, the excited products therefrom also exiting the annular region through the holes in the second electrode into the interior thereof and impinging on the article to be decontaminated or sterilized.

Benefits and advantages of the present invention include an atmospheric-pressure apparatus for sterilizing or decontaminating objects which has superior penetrating capability than low-pressure plasma devices while maintaining exposure temperatures competitive with commercially available low-temperature sterilization devices operating below 60° C., low helium usage, and the ability to prevent the escape of materials detached from the surface of the objects before they are rendered harmless.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIG. 1*a* is a schematic representation of the side view of the atmospheric-pressure plasma decontamination/sterilization chamber of the present invention, while

DETAILED DESCRIPTION

Briefly, the present invention includes a nonthermal, atmospheric-pressure, uniform glow discharge that produces reactive metastable molecular and free-radical species within a confined volume. The reactive species produced in the discharge are rapidly expelled from the discharge volume and onto the surface to be decontaminated, the glow discharge volume and the article being decontaminated being located in a sealed chamber. Decontamination results from the chemical reaction between the reactive species and the surface contaminants through either oxidation or hydrolysis reactions, producing volatile and less hazardous products Ions from the discharge recombine before reaching the surface, thereby reducing damage to the article being processed. The invention has been demonstrated to effectively kill anthrax-surrogate spores and other strains of bacteria, and eliminates the most important limitations of current APPJ technology; those of. escape of re-aerosolized agents or harmful byproducts thereof, and excessive consumption of helium in the feedstock gas. An automated, closed-loop system having the ability to recirculate the plasma gases can be designed.

Figure 1A:
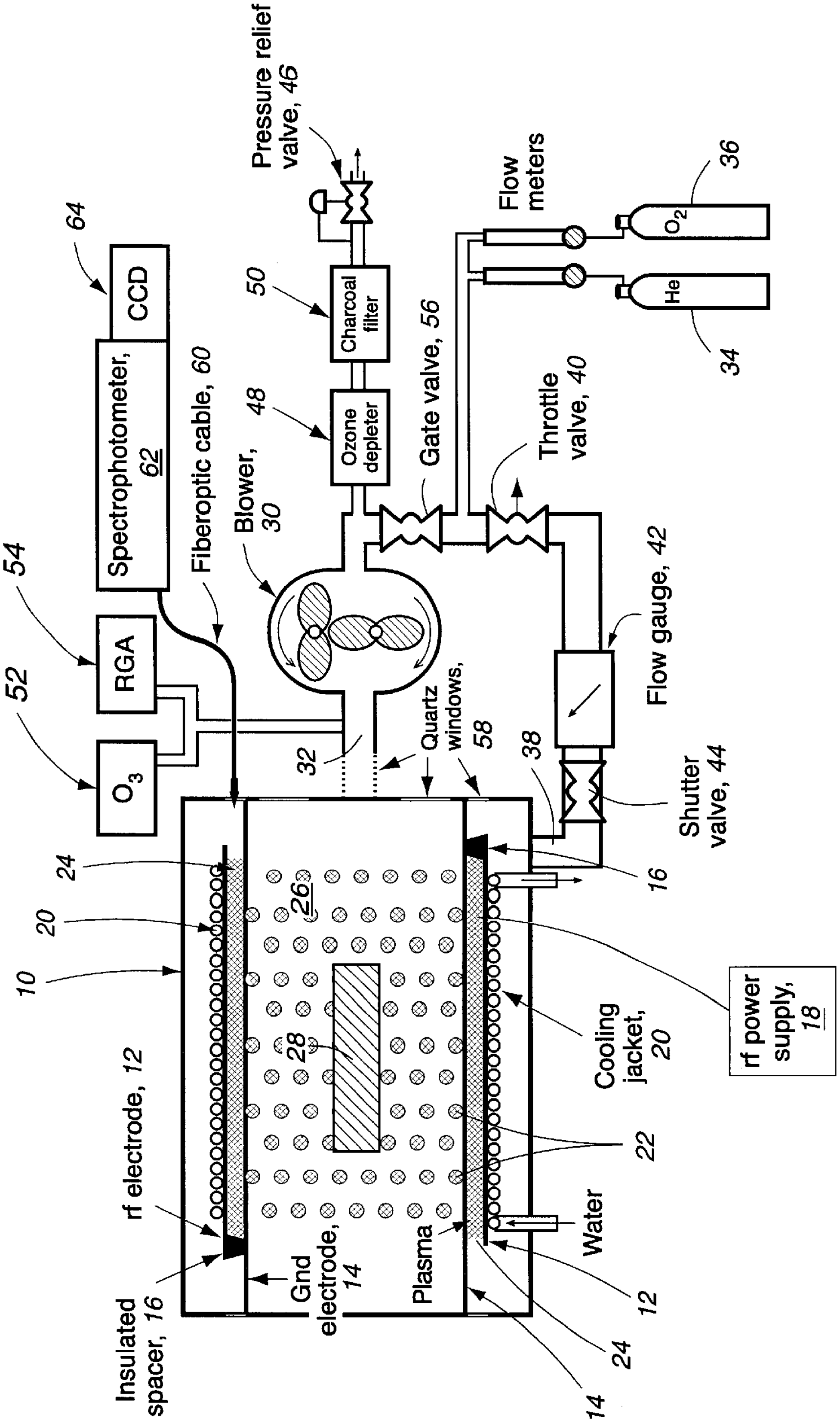

Reference will now be made in detail to the present preferred embodiments of the invention, examples of which are illustrated in the accompanying drawings. Similar or identical structure is labeled using identical callouts. Turning now to the drawings, FIG. 1*a* is a schematic representation of a side view of the decontamination/sterilization chamber of the present invention. Chamber, 10, includes a cylindrical rf electrode, 12, disposed coaxially about a perforated, 6 in. diameter, 10 in. long, grounded cylinder, 14, and spaced apart therefrom using insulating spacers, 16. The spacing employed was 1/16 in.; however, it is expected that the spacing will vary depending on the composition of the plasma gases, rate of flow thereof, and the pressure in the chamber. Rf electrode 12 is powered by a 13.56 MHz rf supply, 18 and water cooled by cooling jacket, 20. The perforations, 22, in grounded cylinder 14 permit reactive species formed in the plasma, 24, generated in the annular region between cylinders 12 and 14 to enter the interior, 26, of chamber 10, where article, 28, to be decontaminated is located. Blower, 30, extracts the plasma gases through port 32 of chamber 10. Plasma gases are introduced directly into the annular region between the electrodes as needed from gas cylinders, 34 and 36, through gas inlet, 38, after passing through throttle valve, 40, and flow gauge, 42, and shutter valve, 44, and removed by blower 30 through pressure relief valve, 46, after passing through ozone remover, 48, and charcoal filter, 50, in order to maintain proper feed gas composition as determined by ozone monitor, 52, and residual gas analyzer, 54.

Figure 1B:
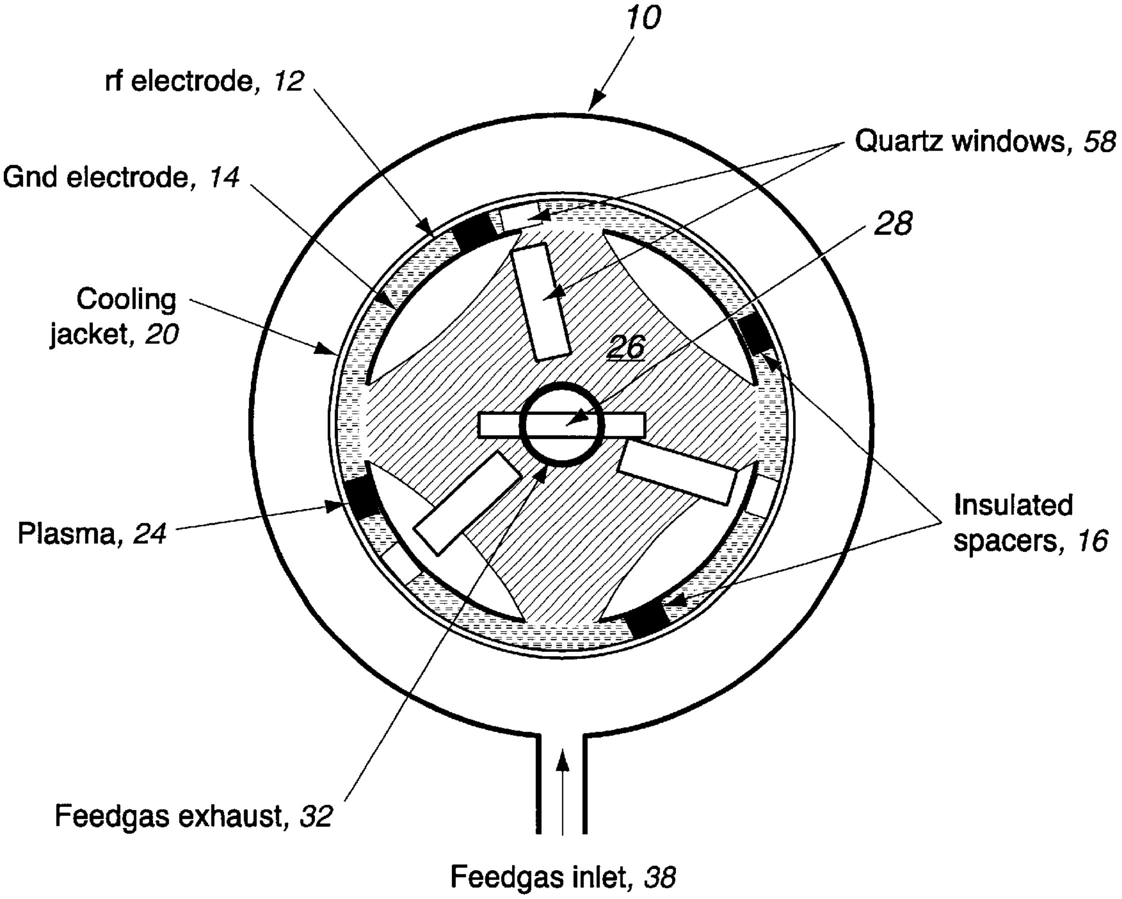
FIG. 1*b* is an end view thereof.

FIG. 1*b* is a schematic illustration of the side view of the chamber shown in FIG. 1*a* hereof. Although only four holes 22 are shown in grounded cylinder 14 for simplicity, the tested apparatus had sixteen holes in each of five rows, for a total of eighty holes. Hole diameter was varied. It was found that ¼ in. holes gave better performance than 1/32 in. holes.

High helium consumption and reaerosolization of chemical agents can be avoided by operating the apparatus of the present invention in a closed configuration and recirculating the feed gas. To initiate plasma operation, the system will be purged of air by first evacuating chamber 10 through port 32 using blower 30 and then flushing the chamber with plasma gases ($He/O_2$) through throttle valve 40 with gate valve, 56, closed and out through pressure relief valve 46, prior to commencing recirculation by opening gate valve 56. The closed recirculating system also allows employment of methods such as pressure reduction and/or pressure pulsing to increase penetration of reactive species into contaminated equipment. By adjusting throttle valve 40, the pressure inside chamber 10 can be varied. The pressure in chamber 10 can be pulsed by rapidly opening and closing shutter valve, 44. Reduced pressure, p, increases the lifetime, τ, of the reactive species according to $\tau \sim p^{-2}$, while pulsing the pressure will enable such species to invade irregular surfaces of the article to be decontaminated or sterilized. The resulting effect is not identical to the operation of a low-pressure plasma, which operates on the order of 0.1 torr and relies on diffusion to transport reactive species, but rather is a true high-pressure discharge which operates on the order of 100 torr where substantial pressure-gradient driven convective flows effectively transport these species.

The combination of heat, vacuum, convection and reactivity should enhance the removal of unwanted agents from surfaces, and agent material that is not adequately neutralized within the chamber will certainly be destroyed as it passes through the discharge during recirculation. It is expected that the present invention will adequately decontaminate and sterilize the inside and outside of sensitive equipment at temperatures<100° C. in about 10 min.

Quartz windows, 58, allow optical access for diagnostics for "endpoint" determination. Previous studies have shown that the energetic, chemical reaction that ensues between atomic oxygen or metastable, molecular oxygen and certain surface contaminants not only results in oxidation (i.e., decontamination of the surface), but can also result in generation of excited states of the reaction products. Often, these excited state species emit light having characteristic wavelengths, such as the 440–480 nm band emission of CO. Phosphorous oxidation products are also expected to emit characteristic spectra. In the present apparatus, feed gases are recirculated through the plasma discharge along with any agent or byproducts which are dislodged from the surface. When these contaminates pass through the plasma discharge, direct impact with energetic plasma electrons will result in enhanced ionization and excitation of these species. Optical emission from the contaminates can be collected by fiber optic cable, 60, directed through spectrophotometer, 62, for analysis, and detected using charge-coupled detector (CCD), 64. The signal derived during decontamination can be used to determine when the decontamination process is complete by the reduction in signal intensity for the selected band spectra. For nerve agents one would detect phosphorous-based reaction products, while for mustard sulfur and chlorine based products would be detected. For biological species, generation of CO emission will be a good monitor of surface organic impurities.

Figure 2:
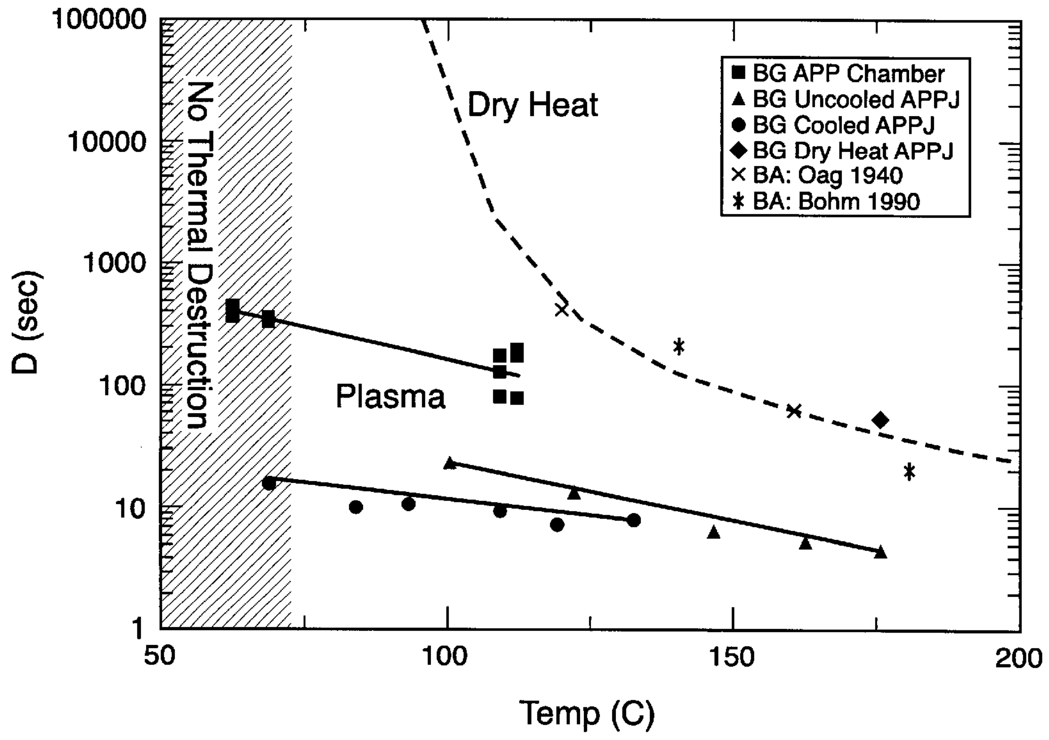
FIG. 2 is a graph of the rate of the reduction in spore viability as a function of temperature for *bacillus globigii* (BG) spores as a result of treatment in accordance with the teachings of the present invention and by other sterilization procedures (for example, *bacillus anthracis* (BA) spores by dry heat).

The chamber described in FIGS. 1*a* and 1*b* was operated as an open system. The results are shown in FIG. 2 hereof, which is a graph of the rate of the reduction in spore viability as a function of temperature for *bacillus globigii* (BG) spores as a result of treatment in accordance with the teachings of the present invention and by other sterilization procedures (for example, *bacillus anthracis* (BA) spores by dry heat). BG spores were located on a platform at the center of the grounded cylindrical electrode, a standoff distance of 3 in. By comparison, results obtained at a standoff distance of 0.2 in. from an APPJ (cooled and uncooled) are shown. The atmospheric-pressure plasma chamber generated D values (the time for a factor of ten reduction in spore viability) about an order of magnitude greater than those obtained using the APPJ, and clearly superior to those using dry heat, particularly at lower temperatures. Below 70° C., there is essentially no thermal kill of the spores. The fact that the present apparatus demonstrates significant spore destruction below this temperature suggests that the mechanism is not purely thermal in nature. Dry heat decontamination results by Oag and Bohm, obtained from the literature are also shown for comparison.

The foregoing description of the invention has been presented for purposes of illustration and description and is not intended to be exhaustive or to limit the invention to the precise form disclosed, and obviously many modifications and variations are possible in light of the above teaching. For example, larger-diameter electrodes would be employed to accommodate more sizable items for processing. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for decontaminating or sterilizing articles which comprises in combination:

(a) a gas-tight chamber;

(b) a first conducting cylindrical electrode disposed within said chamber and having a first axis;

(c) a radiofrequency power supply in electrical contact with said first electrode for providing radiofrequency energy thereto;

(d) a second conducting cylindrical electrode disposed within said first electrode having a second axis colinear with the first axis and capable of receiving the article to be decontaminated or sterilized within the interior thereof, whereby an annular region is formed between said first electrode and said second electrode, said second electrode being maintained at ground potential and further having holes formed through the cylindrical surface thereof; and (e) means for introducing gases into said chamber such that the introduced gas flows directly into the annular region and exits this region through the holes in said second electrode, whereby a uniform radiofrequency electrical discharge is caused to occur in the gas flowing through the annular region as a result of the radiofrequency energy having been applied to said first electrode, the excited products therefrom also exiting the annular region through the holes in said second electrode into the intenor thereof and impinging on the article to be decontaminated or sterilized.

2. The apparatus for decontaminating or sterilizing articles as described in claim 1, further comprising means for extracting gases from the interior of said second electrode.

3. The apparatus for decontaminating or sterilizing articles as described in claim 2, further comprising means for recirculating the gases between said means for introducing gases into said chamber and said means for extracting gases from the interior of said second electrode.

4. The apparatus for decontaminating or sterilizing articles as described in claim 2, wherein said means for extracting gases from the interior of said second electrode permits the pressure in said chamber to be lowered below one atmosphere.

5. The apparatus for decontaminating or sterilizing articles as described in claim 2, wherein said means for introducing gases into said chamber and said means for extracting gases from the interior of said second electrode maintain the gas pressure within said chamber such that substantially no ions generated in the electrical discharge impinge upon the article to be decontaminated.

6. The apparatus for decontaminating or sterilizing articles as described in claim 1, further comprising means for cooling said first electrode.

7. The apparatus for decontaminating or sterilizing articles as described in claim 1, wherein said means for introducing gases into said chamber permits the pressure in said chamber to be pulsed.

8. The apparatus as described in claim 1, wherein the radiofrequency is 13.56 MHz and the introduced gases include helium and oxygen.

* * * * *